United States Patent
Fenske

(10) Patent No.: US 9,439,814 B2
(45) Date of Patent: *Sep. 13, 2016

(54) ELASTIC ABSORBENT SANITARY ARTICLE FOR ABSORBING BODILY FLUIDS

(75) Inventor: Wilfried Fenske, Wadenswil (CH)

(73) Assignee: Evonik Degussa GmbH, Essen (DE)

( * ) Notice: Subject to any disclaimer, the term of this patent is extended or adjusted under 35 U.S.C. 154(b) by 90 days.

This patent is subject to a terminal disclaimer.

(21) Appl. No.: 14/112,056

(22) PCT Filed: Apr. 27, 2012

(86) PCT No.: PCT/EP2012/057833
§ 371 (c)(1),
(2), (4) Date: Nov. 6, 2013

(87) PCT Pub. No.: WO2012/146748
PCT Pub. Date: Nov. 1, 2012

(65) Prior Publication Data
US 2014/0052089 A1    Feb. 20, 2014

(30) Foreign Application Priority Data

Apr. 28, 2011 (DE) .......................... 10 2011 018 985

(51) Int. Cl.
*A61F 13/15* (2006.01)
*A61F 13/532* (2006.01)
(Continued)

(52) U.S. Cl.
CPC .............. *A61F 13/5323* (2013.01); *B32B 5/04* (2013.01); *B32B 5/26* (2013.01); *B32B 7/02* (2013.01);
(Continued)

(58) Field of Classification Search
CPC ............. A61F 13/5323; A61F 13/535; A61F 13/530562; B32B 27/00; B32B 27/02; B32B 27/12; B32B 27/24; B32B 27/28; B32B 5/00; B32B 5/04; B32B 5/12; B32B 5/22; B32B 5/26; B32B 7/02; B32B 7/10
See application file for complete search history.

(56) References Cited

U.S. PATENT DOCUMENTS 4,227,952 A    10/1980   Sabee
4,753,643 A     6/1988   Kassai
(Continued)

FOREIGN PATENT DOCUMENTS

CN    1303255    7/2001
CN    1349787    5/2002
(Continued)

OTHER PUBLICATIONS

Buchholz, Frederick L. and Graham, Andrew T., "Modern Superabsorbent Polymer Technology," copyright 1998, John Wiley & Sons, Inc., Chapter 1: "Absorbency and Superabsorbency," pp. 1-17 (19 pages).

(Continued)

*Primary Examiner* — Bradley Philips
(74) *Attorney, Agent, or Firm* — Bernard Lau; Linda S. Li; Jason S. Ngul

(57) ABSTRACT

An absorbent hygiene product for acquiring fluids, having a flexurally yielding topsheet and a flexurally yielding backsheet, has, disposed between these sheets, an absorbent laminate, which in turn has two flexurally yielding outer plies, arranged adheringly between which are at least two diagonally intersecting, pre-tensioned plies of elastic filaments, a quantity of a superabsorbent polymer being incorporated in each of the discrete sections thus formed, and the topsheet-side outer ply of the laminate consists of a hydrophobic material, and the backsheet-side outer ply of the laminate consists of a hydrophilic material.

10 Claims, 2 Drawing Sheets

(51) Int. Cl.
*B32B 5/04* (2006.01)
*B32B 5/26* (2006.01)
*B32B 7/02* (2006.01)
*B32B 27/12* (2006.01)
*B32B 27/28* (2006.01)

(52) U.S. Cl.
CPC ............... *B32B 27/12* (2013.01); *B32B 27/28* (2013.01); *B32B 2307/728* (2013.01); *B32B 2555/02* (2013.01)

(56) References Cited

U.S. PATENT DOCUMENTS

| | | | |
|---|---|---|---|
| 4,886,511 | A | 12/1989 | Korpman |
| 5,226,992 | A | 7/1993 | Morman |
| 5,275,676 | A | 1/1994 | Rooyakkers et al. |
| 5,336,545 | A | 8/1994 | Morman |
| 5,366,452 | A | 11/1994 | Widlund et al. |
| 5,411,497 | A | 5/1995 | Tanzer et al. |
| 5,425,725 | A | 6/1995 | Tanzer et al. |
| 5,433,715 | A | 7/1995 | Tanzer et al. |
| 5,451,219 | A | 9/1995 | Suzuki et al. |
| 5,505,718 | A | 4/1996 | Roe et al. |
| 5,514,470 | A | 5/1996 | Haffner et al. |
| 5,562,646 | A | 10/1996 | Goldman et al. |
| 5,593,399 | A | 1/1997 | Tanzer et al. |
| 5,601,542 | A | 2/1997 | Melius et al. |
| 5,643,238 | A | 7/1997 | Baker |
| 5,843,059 | A | 12/1998 | Niemeyer et al. |
| 5,938,659 | A | 8/1999 | Tu et al. |
| 5,964,743 | A | 10/1999 | Abuto et al. |
| 6,068,620 | A | 5/2000 | Chmielewski |
| 6,129,717 | A | 10/2000 | Fujioka et al. |
| 6,149,638 | A | 11/2000 | Vogt et al. |
| 6,231,557 | B1 | 5/2001 | Krautkramer et al. |
| 6,362,389 | B1 | 3/2002 | McDowall et al. |
| 6,420,625 | B1 | 7/2002 | Jones et al. |
| 6,429,350 | B1 | 8/2002 | Tanzer et al. |
| 6,570,056 | B1 | 5/2003 | Tanzer et al. |
| 6,582,413 | B2 | 6/2003 | Krautkramer et al. |
| 6,602,234 | B2 | 8/2003 | Klemp et al. |
| 6,610,900 | B1 | 8/2003 | Tanzer |
| 6,632,209 | B1 | 10/2003 | Chmielewski |
| 6,646,178 | B2 | 11/2003 | Furuya et al. |
| 6,646,180 | B1 | 11/2003 | Chmielewski |
| 6,682,512 | B2 | 1/2004 | Uitenbroek et al. |
| 6,790,202 | B2 | 9/2004 | Klemp et al. |
| 6,855,223 | B2 | 2/2005 | Johnson |
| 6,972,011 | B2 | 12/2005 | Maeda et al. |
| 7,037,300 | B2 | 5/2006 | Kling |
| 7,175,910 | B2 | 2/2007 | Ehrnsperger et al. |
| 7,247,152 | B2 | 7/2007 | Klemp et al. |
| 7,361,246 | B2 | 4/2008 | Chang et al. |
| 7,744,576 | B2 | 6/2010 | Busam et al. |
| 7,750,203 | B2 | 7/2010 | Becker et al. |
| 9,056,033 | B2 * | 6/2015 | Fenske ............... A61F 13/15593 |
| 2002/0095127 | A1 | 7/2002 | Fish et al. |
| 2002/0102392 | A1 | 8/2002 | Fish et al. |
| 2002/0115969 | A1 | 8/2002 | Maeda et al. |
| 2003/0082966 | A1 | 5/2003 | Menday et al. |
| 2003/0225382 | A1 | 12/2003 | Tombult-Meyer et al. |
| 2004/0087923 | A1 | 5/2004 | Cole |
| 2004/0110325 | A1 | 12/2004 | Nanni et al. |
| 2006/0206073 | A1* | 9/2006 | Crane ............... A61F 13/5323 604/378 |
| 2008/0156418 | A1* | 7/2008 | Fenske ............... A61F 13/15593 156/161 |
| 2009/0043273 | A1* | 2/2009 | Carlucci ............... A61F 13/5323 604/370 |
| 2013/0011601 | A1 | 1/2013 | Fenske |
| 2013/0012899 | A1* | 1/2013 | Fenske ............... A61F 13/15593 604/365 |

FOREIGN PATENT DOCUMENTS

| | | |
|---|---|---|
| DE | 102004026070 A1 | 12/2005 |
| DE | 102010013288 A1 | 9/2011 |
| EP | 724418 A1 | 8/1996 |
| EP | 0803602 A1 | 10/1997 |
| GB | 2181036 A | 4/1987 |
| JP | 2002192641 A | 7/2002 |
| WO | 9511654 A1 | 5/1995 |
| WO | 9949826 A1 | 10/1999 |
| WO | 0035503 A1 | 6/2000 |
| WO | 0134082 A1 | 5/2001 |
| WO | 03041627 A2 | 5/2003 |
| WO | 03106162 A1 | 12/2003 |
| WO | 2004011046 A1 | 2/2004 |
| WO | 2004071363 A1 | 8/2004 |
| WO | 2004071539 A2 | 8/2004 |

OTHER PUBLICATIONS

Buchholz, Frederick L. and Graham, Andrew T., "Modern Superabsorbent Polymer Technology," copyright 1998, John Wiley & Sons, Inc., Chapter 2: "Chemistry of Superabsorbent Polyacrylates," pp. 19-67 (51 pages).

Buchholz, Frederick L. and Graham, Andrew T., "Modern Superabsorbent Polymer Technology," copyright 1998, John Wiley & Sons, Inc., Chapter 3: "Commercial Processes for the Manufacture of Superabsorbent Polymers," pp. 69-117 (51 pages).

Buchholz, Frederick L. and Graham, Andrew T., "Modern Superabsorbent Polymer Technology," copyright 1998, John Wiley & Sons, Inc., Chapter 4: "Analysis and Characterization of Superabsorbent Polymers," pp. 119-165 (49 pages).

Buchholz, Frederick L. and Graham, Andrew T., "Modern Superabsorbent Polymer Technology," copyright 1998, John Wiley & Sons, Inc., Chapter 5: "The Structure and Properties of Superabsorbent Polyacrylates," pp. 167-221 (57 pages).

Fenske, U.S. Appl. No. 11/569,454, filed Jun. 6, 2007, Non-Final Office Action dated Jan. 21, 2010 (9 pages).

Fenske, U.S. Appl. No. 11/569,454, filed Jun. 6, 2007, Final Office Action dated Jul. 22, 2010 (8 pages).

German language International Search Report mailed on Jul. 12, 2012 in PCT/EP2012/057833 (4 pages).

German language Written Opinion mailed on Jan. 13, 2012 in PCT/DE2011/000338 (8 pages).

German language Written Opinion mailed on Jan. 13, 2012 in PCT/DE2011/000339 (8 pages).

International Search Report mailed on Jan. 13, 2012 in PCT/DE2011/000338 (3 pages).

International Search Report mailed on Jan. 13, 2012 in PCT/DE2011/000339 (3 pages).

International Search Report mailed on Jul. 12, 2012 in PCT/EP2012/057833 (3 pages).

* cited by examiner

ELASTIC ABSORBENT SANITARY ARTICLE FOR ABSORBING BODILY FLUIDS

This application is a national stage application under 35 U.S.C. §371 of International Application No. PCT/EP2012/057833 filed 27 Apr. 2012, which claims priority to German Application No. DE 10 2011 018 985.8 filed 28 Apr. 2011, the disclosures of which are expressly incorporated herein by reference.

FIELD

The invention relates to an elastic, absorbent hygiene article for acquiring body fluids, having a flexurally yielding topsheet and a flexurally yielding backsheet, inserted adheringly between which is an absorbent laminate, the absorbent laminate consisting of two flexurally yielding outer plies, incorporated adheringly between which are at least two diagonally intersecting, pre-tensioned plies of elastic filaments, with discrete sections of superabsorbent polymer being incorporated in the laminate.

BACKGROUND

Modern hygiene articles for acquiring body fluids, such as urine, perspiration, menstrual bleeding or secretions from wounds, are based in principle on a layered sequence of a plurality of plies of functional, flexurally yielding materials which, in appropriate form, acquire the discharged fluid from the emission site and distribute it, store it and close it off with respect to the exterior. Efforts are made additionally to minimize wetting back to the skin of the wearer, and suitable elastic elements, such as elastic closure systems and specific elastication of individual regions, are used with the aim of optimum conformity to the user's anatomy.

This procedure is encountered consistently in the development of a very wide variety of hygiene and medical articles, such as, for instance, infant nappies, sanitary towels, incontinence products, dressing materials, clinical absorption material, packaging material for foods, etc.

It is fundamentally desirable to optimize the number and quantity of the materials for fulfilling this function in order to achieve economic and environmental rationalization not only of the levels of material and energy employed in the production of these products but also of the volume of the product and hence its storage, distribution and disposal requirement.

Products with the function described above consist in principle of a first outer ply (topsheet) facing the skin of the wearer and intended to have skin-kindly qualities; an opposite, second outer ply (backsheet) intended to provide security against unwanted emergence of fluid into clothing or the surrounding area; and also, incorporated therein, an absorption core for the absorption and storage of the body fluid. This absorption core is intended to fulfill the functions of rapid fluid acquisition, rapid transverse distribution in the product, and reliable storage of the fluid in the absorption core, with the ultimate aim of minimal wetting back by the fluid acquired in the absorption core.

In the products known from the art, the function of fluid acquisition is achieved by plies of rapidly fluid-conducting materials, such as, for instance, lightweight, bulky spunbonded nonwovens or needle-punched felts based on polyester, polypropylene or polyethylene; the function of distributing the fluid in the absorption core is achieved by cellulosic fibers, cellulose or chemically modified cellulosic fibers ("Curly fibers"); and the function of fluid storage is achieved by superabsorbent polymers. It is in the nature of the matter that here, owing to the multiple effect of the individual materials, there is a partial overlap of functions. It is also obvious that materials which are able effectively to transport and conduct fluids fulfill this transport function, normally, equally in all directions. Effective transport and conduct of fluid away from the skin side in the direction of the absorption core therefore generally implies a comparably effective transport and conduct effect back in the direction of the skin side of the wearer, which promotes unwanted back-wetting.

It is therefore considered an object of the present invention to configure a hygiene article of the generic type specified at the outset in such a way that the properties of the hygiene article are improved with minimal cost and deployment of material and manufacture. Here, where possible, the storage of fluid is to be ensured very rapidly and reliably, and at the same time the risk of back-wetting is to be reduced.

SUMMARY

The present invention includes various embodiments as set forth herein. In one embodiment, the present invention is directed to an absorbent hygiene product for acquiring fluids, formed at least of a flexurally yielding topsheet and a flexurally yielding backsheet, inserted adheringly between which is an absorbent laminate, consisting of two flexurally yielding outer plies, incorporated adheringly between which are at least two diagonally intersecting, pre-tensioned plies of elastic filaments, and into which discrete sections of superabsorbent polymer have been incorporated, characterized in that the topsheet-side outer ply of the laminate is a hydrophobic material which in the region of the adherence with the elastic filaments and the second outer ply has been locally or sectionally made fluid-pervious mechanically, chemically or thermally.

DETAILED DESCRIPTION

This object is achieved in accordance with the invention in that the topsheet-side outer ply of the laminate is a hydrophobic material which in the region of the adherence with the elastic filaments and the second outer ply has locally or sectionally been made liquid-previous mechanically, chemically or thermally. In contrast to the hygiene products known from the art, the outer ply of the laminate, which faces the topsheet and hence the skin side of the hygiene product, is not optimized for rapid liquid acquisition and distribution, but instead, entirely oppositely, is given a hydrophobic design, in order to counteract unwanted back-wetting that might be caused by the transport of the fluid initially acquired in the laminate back towards the skin side. This back-wetting is very largely prevented by the hydrophobic qualities of the outer ply of the laminate, facing the topsheet. The laminate of the invention supports improved fluid acquisition by the superabsorbent polymer material.

In accordance with one advantageous embodiment of the concept of the invention, the topsheet-side outer ply of the laminate has a high barrier effect for fluids.

The examples which follow serve for further illustration of the qualities of the hygiene products of the invention. The experiments performed for this purpose used and investigated the nonwoven materials below, which are identified below only using the abbreviated designation indicated in each case:

| Abbreviated designation | Designation | Manufacturer | Grammage | Quality |
|---|---|---|---|---|
| Corovin | PC 5FF-111 | Corovin GmbH; Peine, Germany | 17 gsm | hydrophobic |
| Fibrella | Fibrella 30 | Suominen Nonwovens Ltd.; Nakkila, Finland | 30 gsm | hydrophilic |
| Novellin | Novellin 23 | Suominen Nonwovens Ltd.; Nakkila, Finland | 23 gsm | hydrophilic |
| Pegas | Pegatex 13 | Pegas nonwovens s.r.o.; Znojmo, Czech Republic | 13 gsm | hydrophobic |

In each case, a number of specimens of these nonwoven materials were investigated for those properties—such as, for example, barrier effect and spreading—that are relevant for the present invention.

EXAMPLE 1

Determination of the Barrier Effect

In order to be able to determine the barrier effect of a nonwoven material in a suitable way, the height of a column of liquid over the nonwoven was determined for different nonwovens.

The test apparatus used was a transparent liquid-rise column having a length of 50 cm and an internal diameter of 1.2 cm (external diameter 1.6 cm), which carried a continuous scale in 0.1 cm steps. Each of the test specimens used was a square nonwoven specimen with an edge length of 6 cm. The test liquid used was a 0.9% strength NaCl solution. Using a tube clamp or a rubber ring, the nonwoven specimen is fixed at the bottom end of the liquid-rise column, with an orientation such that the possibly rougher side of the nonwoven specimen faces in the direction of the liquid-rise column. The position to be selected here for the clamping ring or rubber ring is 1 cm above the bottom tube end of the liquid-rise column, and the nonwoven specimen must be fixed on the tube in such a way that there is no liquid egress above the clamping ring during the test procedure. A calibrated pump (e.g. Ismatec MCP ISM 404B) is used to add the test solution to the liquid-rise column with a feed rate of 60 g/min. The bottom end of the feed line of the pump should be set 20 cm above the nonwoven specimen. Simultaneously with the start of the pump, time measurement also begins. The height of the liquid that forms above the specimen in the liquid-rise column, or the height of the liquid level, is read off at the point of first drop breakthrough by test liquid and also after 1, 2, 3, 4, and 5 minutes in each case.

The overview below shows the average level heights after 5 minutes, or 300 seconds, the average values reported being averaged over 5 measurements in each case:

|  | Time [s] | Ø height [cm] |
|---|---|---|
| Fibrella | 300 | 0.1 |
| Novellin | 300 | 0.2 |
| Pegas | 300 | 3.3 |
| Corovin | 300 | 11.5 |

It is apparent that hydrophobic nonwovens such as, for example, Corovin or Pegas exhibit a significantly higher liquid level height than other nonwovens (for example Fibrella or Novellin). The barrier effect of the hydrophobic nonwovens, accordingly, is much better than the barrier effect of the hydrophilic nonwovens. This barrier effect of the topsheet-side outer ply is authoritatively responsible for the low back-wetting qualities of the laminate of the invention. It has emerged, surprisingly, that contrary to the prejudice among those in the art, in spite of a good barrier effect on the part of the topsheet-side outer ply, it is possible to enable rapid liquid acquisition and large-area distribution within the laminate, and the barrier effect of the topsheet-side outer ply does not fundamentally rule out these additionally required qualities.

For the present invention, a good barrier effect is assumed when the measured average liquid level height is more than 2 cm.

A very good barrier effect is assumed when the measured average liquid level height is more than 5 cm. In accordance with one particularly advantageous embodiment of the concept of the invention, therefore, the topsheet-side outer ply of the laminate has a very good barrier effect, i.e. a liquid column of more than 5 cm, preferably of more than 8 cm and with more particular preference of more than 10 cm, when the determination of the liquid level heights that is elucidated in more detail above is carried out.

In order to support the distribution and rapid acquisition of a relatively large quantity of fluid within the laminate, the invention further provides for the backsheet-side outer ply of the laminate to be a hydrophilic material with good fluid transport quality.

Advantageously here, the backsheet-side outer ply of the laminate is a hydrophilic material featuring high areal distribution of a fluid drop applied virtually pointwise.

EXAMPLE 2

Determination of the Areal Distribution Qualities

In order to characterize the areal distribution qualities of a fluid applied to a nonwoven material, the spreading was determined for various nonwovens in accordance with the experimental procedure described below. The test apparatus used was an inner plastic ring having an external diameter of 9 cm (height 8 cm, internal diameter 8.2 cm) and also an outer plastic ring having an internal diameter of 9.2 cm. The test specimens used were square nonwoven specimens with an edge length of 15 cm. The test fluid used was a 0.9% strength NaCl solution colored using Patent Blue (0.8 g per 100 g of NaCl solution). The nonwoven specimen is placed centrally onto the smaller plastic ring and is fixed by inserting one of the two rings into the other. In this arrangement, the possibly rougher side of the nonwoven specimen is oriented to the top (towards the application of fluid). Using an Eppendorf pipette, 1 ml of the test solution is cautiously applied centrally to the nonwoven specimen at an angle of about 30°. After a waiting time of 20 minutes, any of the test fluid that has remained on the nonwoven specimen is removed with a pipette. The nonwoven specimens are subsequently dried at 30° C. for 4 hours. To determine the area wetted, the dried nonwoven specimen is photocopied and the wetted region (which appears dark on the photocopy) is determined by being cut out and weighed (basis weight of the paper 0.01 g/cm$^2$).

The overview below indicates the average size of the area of the nonwoven specimen that is wetted by the quantity of fluid, averaged over 4 measurements in each case:

|  | Area wetted [cm²] |
|---|---|
| Fibrella | 57.0 |
| Novellin | 20.5 |
| Corovin | 2.1 |
| Pegas | 1.8 |

It was evident that certain hydrophilic nonwovens such as, for example, Fibrella or Novellin have a significantly better fluid distribution property than other nonwovens such as, for example, Corovin or Pegas.

In connection with the present invention, a high areal distribution of a fluid applied to the nonwoven material is assumed when the fluid quantity of 1 ml applied to the nonwoven material is distributed on average over a wetted area of more than 10 cm².

A very high areal distribution is assumed when the fluid quantity applied to the nonwoven material is distributed on average over a wetted area of more than 20 cm². In accordance with one particularly advantageous embodiment of the concept of the invention, therefore, provision is made for the fluid quantity applied to the nonwoven material to be distributed on average over a wetted area of more than 20 cm², preferably more than 40 cm² and more preferably more than 55 cm², when the determination of the liquid distribution as elucidated in more detail above is carried out.

For the purpose of determining a particularly advantageous inventive embodiment of the absorbent laminate, experiments were carried out, in each of which the fluid acquisition and back-wetting were determined and investigated for different combinations of hydrophilic and hydrophobic materials for the outer plies of the laminate.

EXAMPLE 3

Determination of the Characteristic Qualities of Different Absorbent Laminates

A relatively large number of substantially similar test specimens were produced for an absorbent hygiene product having the features relevant to the invention, using in each case identically coincident topsheets and backsheets. The absorbent laminates inserted and fixed therein differ only in terms of the particular materials used for the topsheet-side outer ply and for the backsheet-side outer ply. Otherwise, the constructions of the absorbent laminates, including their dimensions and the superabsorbent polymer materials used, are identically coincident.

In order to produce the absorbent laminates, two pin rails 1200 mm long were arranged in a clamping frame at a distance of 160 mm from one another. Arranged on each pin rail is a row of 24 pins at a distance of 45 mm from one another. An elastic yarn (615 dtex, 550 den, Dorlastan) was passed, without pre-tension, beginning from a 1st pin on one end of the first pin rail diagonally to the 10th pin of the opposite pin rail, wound around the laterally adjacent 11th pin of this opposite pin rail, passed diagonally back to the 2nd pin of the first pin rail and then passed to the laterally adjacent 3rd pin of the first pin rail. In this way, two diagonally extending parallel yarn sections were produced between the two pin rails. Starting from the 3rd pin of the first pin rail, this procedure was repeated up to the penultimate pin of the opposite pin rail, thereby producing 14 yarn sections extending parallel to one another and diagonally between the two pin rails. Following this, the elastic yarn was passed to the last pin of the opposite pin rail and then to the last pin of the first pin rail, in order to produce, starting from this pin, a mirrored yarn profile back to the 1st pin of the opposite pin rail. The yarn then forms two crossed plies between the two pin rails, each consisting of yarn sections extending parallel to one another and diagonally with the same inclination between the pin rails.

The two pin rails are pulled apart to a distance of 390 mm from one another, and the yarn sections, or the entire yarn, are/is tensioned. The two crossed plies of the yarn sections then form a honeycomb-like specimen, with the individual combs having a size of approximately 30 mm×30 mm.

Using a glue gun (glue gun HB 700 from Bühnen, with a hotmelt nozzle from Bühnen, pressure about 2.5 bar, glue Bostik 2052 FUN from Bostik), a glue quantity of about 1.7 g is sprayed uniformly onto the tensioned yarn sections at a spraying angle of 45° within one minute. Glue strings hanging down from the underside of the yarn sections are carefully removed by hand.

Placed on a marble plate is a first outer ply, of Corovin, for example, with dimensions of 300 mm×500 mm, followed by a perforated metal plate (250 mm×500 mm with 72 drilled holes each with a distance of 45 mm from one another, or a 45/405 hole pattern). The holes of the perforated plate are adapted to the arrangement of the honeycombs of the crossed plies of the yarn sections, and so each honeycomb is associated, approximately centrally, with a hole of the perforated plate.

12.5 g of a superabsorbent polymer material are weighed out on a laboratory balance and distributed uniformly, using a doctor blade or a spatula, into the holes of the perforated plate. The excess superabsorbent polymer material is removed, and then the perforated plate is lifted up.

Following this, the tension frame with the crossed plies of the elastic yarn sections is placed over the first outer ply with the portions of superabsorbent polymer material distributed thereon, it being important to ensure a central arrangement of the superabsorbent polymer material within the individual combs, and a corresponding orientation of the tensioning frame.

A second outer ply, of Fibrella, for example, having the same dimensions as the first outer ply is placed carefully onto the crossed plies of the yarn sections and is rolled over or pressed on horizontally and diagonally using a commercial foam roller, causing the two outer plies to be joined to one another and adhesively bonded by the crossed plies, located between them, of the yarn sections provided with glue. Formed between the individual yarn sections are closed cassettes, each containing an equal-size portion of the superabsorbent polymer material.

A cutting template with dimensions of 220 mm×500 mm is placed onto the absorbent laminate produced in this way, and the laminate is cut to this size, care being taken to ensure that there is no cutting into cassettes with superabsorbent polymer material and no emergence of superabsorbent polymer material.

In order to produce a test specimen of a nappy-like absorbent hygiene product with this absorbent laminate, two metal rails are fastened on a first metal plate at a distance of 125 mm. Mounted on each of the two metal rails are six metal pins, around which an elastic yarn (615 dTex, 550 den, Dorlastan) is placed without tension, producing the following pattern of parallel threads of the yarn. A first group of 3 parallel threads is formed, with a distance of 5 mm from one another, followed at a distance of 50 mm by a second group of 2 parallel threads, the 2 threads in this group also each having a distance of 5 mm from one another. Following at a distance of 65 mm is a third group, again formed of 2 parallel threads, each of which extends at a distance of 5 mm from the other. The thread pattern is completed by a fourth group of 3 parallel threads, at a distance of 5 mm from one another. The fourth group follows in turn, at a distance of 50 mm, from the third group. The distance from group 1 to group 4 here in total is 190 mm. The two metal rails are taken off and fixed on a second metal plate of 400 mm×600 mm with a distance of 520 mm from one another, the threads being pre-tensioned as a result. Below thread groups 1 and 2 and also 3 and 4, in each case, a strip of Corovin (160 mm×520 mm) is placed onto the metal plate in such a way that the longitudinal direction of the two strips of Corovin coincides with the orientation of the thread groups, and the center in the longitudinal direction of each Corovin strip is oriented below the inner assigned thread group 2 or 3, respectively. The two Corovin strips overlap here between the inner thread groups. The yarn sections are sprayed with glue at those points relevant for the gluing of the yarn threads (glue gun HB 700 from Bühnen with a hotmelt nozzle from Bühnen, pressure about 2.5 bar, glue Bostik 2052 FUN from Bostik). Subsequently, one after another, each of the Corovin strips is likewise sprayed with glue, folded from inside to outside along the middle in longitudinal direction, so that the folded halves and the two longitudinal edges of each Corovin strip that are now located on the outside come to lie congruently one above another, and each folded Corovin strip surrounds the thread groups 1 and 2 or 3 and 4 assigned to it. The halves of the Corovin strips that lie one above another are pressed against one another and adhesively bonded to one another.

The folded Corovin strips are sprayed with glue and pulled apart to some extent, and so the longitudinal edges facing one another have a distance of 90 mm from one another. Subsequently a topsheet (170 mm×520 mm, Novellin) is placed on and is pressed onto the Corovin strips, and bonded adhesively to them, along the side edges.

The middle region of the topsheet is glued along the later marginal region of the absorbent laminate to be bonded adhesively to it, and is glued with misting within the marginal region. The outer ply of the absorbent laminate, this ply later facing the topsheet, is likewise glued. In the middle region of the topsheet, the absorbent laminate is placed on, with the absorbent laminate being pulled apart at 400 mm×120 mm and placed by the topsheet-facing outer ply onto the topsheet.

This is followed by gluing of the absorbent laminate, the end tabs, and a glued margin. Finally, the backsheet (RKW Hypor B 140 textile film, type 45755, white, with dimensions of 210 mm×520 mm) is placed on and fixed, or pressed on using a foam roller.

For the procedure of the experiments, a number of test specimens of absorbent hygiene products were produced, each differing only in the nonwoven material of the outer plies of the absorbent laminate. 4 identical test specimens were produced for each investigated combination of nonwoven materials for the outer plies of the absorbent laminate.

For the determination of the penetration time, a quantity of 70 ml of a 0.9% strength sodium chloride solution was applied through a funnel within 10 seconds centrally to the topsheet of each test specimen of the absorbent hygiene product, this process being carried out four times in succession with an interval. The funnel consists of a Makrolon sheet (400 mm×300 mm×10 mm) with a centrally disposed filling port (44 mm internal diameter, 80 mm high) and a total weight of 940 g. The funnel was weighted on opposite end faces with two rectangular weights each weighing 3800 g.

The penetration time is defined as the time duration taken for the fluid, following complete filling, to have penetrated completely in the test specimen, with no more fluid being present in the filling port.

If fluid emerges at any point of the absorbent hygiene product during or after one of the four successive applications of fluid, the test is discontinued. In this case, the test specimen in question is considered unsuitable, since the fluid was not fully acquired and retained.

For the determination of the back-wetting, a multi-ply stack of filter papers with a total weight of at least 3.5 g was placed on both sides at a distance of 8 cm from the middle of the test specimen, 20 minutes in each case after each application of fluid, and each of these stacks was weighted with a circular weight of 1200 g. The filter paper comprises circular Macherey-Nagel filter papers, MN 617, having a diameter of 90 mm. After 2 minutes, the weights and the filter paper stacks are removed. The back-wetting is determined as a sum total "total back-wetting" of the two differential weights, "back-wetting 1" and "back-wetting 2" of the two filter-paper stacks after the weight-loaded application time of 2 minutes on the fluid-filled absorbent hygiene product, minus the dry weight of the filter-paper stack.

The experiments and measurements carried out in each case for at least 4 test specimens of the same kind produced on average the following results for the penetration time and the back-wetting after the fourth and last application of fluid:

| Topsheet-side outer ply | Backsheet-side outer ply | Penetration time [s] | Back-wetting 1 [g] | Back-wetting 2 [g] | Back-wetting, total [g] | Liquid emergence |
| --- | --- | --- | --- | --- | --- | --- |
| Fibrella | Fibrella | 47.0 | 3.19 | 0.70 | 3.89 | no |
| Novellin | Novellin | 42.0 | 3.10 | 1.76 | 4.86 | no |
| Corovin | Corovin | — | — | — | — | yes |
| Pegas | Pegas | — | — | — | — | yes |
| Fibrella | Corovin | 38.0 | 2.15 | 4.31 | 6.28 | no |
| Corovin | Fibrella | 30.7 | 0.11 | 0.11 | 0.22 | no |

These experiments show that, in accordance with expectations, a rapid acquisition of fluid (short penetration time, in the region of about 45 seconds) is achieved when using a hydrophilic nonwoven material such as Fibrella or Novellin, for example, for the two outer plies of the laminate. However, the hydrophilic nonwoven materials do not offer convincing protection from back-wetting, which is why in each case about 3.9 g and, respectively, 4.9 g were determined as differential weights for the total back-wetting.

The hydrophobic nonwoven materials investigated, such as Corovin or Pegas, for example, led in each case to the emergence of fluid during or immediately after the application of fluid. An absorbent hygiene product with an absorbent laminate of this kind, or with two outer plies of these hydrophobic nonwoven materials, appears not to be suitable and is unable, unlike other nonwoven materials, to prevent unwanted fluid emergence.

Nor does the combination of a topsheet-side outer ply made from a hydrophilic material (Fibrella, for example) and a backsheet-side outer ply made from a hydrophobic material (Corovin, for example) provide convincing results. The penetration time, at 38 seconds, is comparatively short, and yet there is very high back-wetting, with about 6.3 g fluid acquisition in the filter paper.

Surprisingly, the experiments have shown that the combination of a topsheet-side outer ply made of a hydrophobic material (Corovin, for example) and a backsheet-side outer ply made of a hydrophilic material (Fibrella, for example) yields the best results. In spite of the hydrophobic nonwoven material used for the topsheet-side outer ply of the absorbent laminate, it is possible to achieve a very rapid penetration time of about 31 seconds. The rapid penetration is promoted by the structure of the absorbent laminate, and/or by the transport channels formed between the individual cassettes or combs with superabsorbent polymer material, these channels being formed in the course of the above-described production of the laminates. Moreover, the total back-wetting is only 0.22 g and is therefore better by more than one order of magnitude than all other back-wetting values for other combinations of nonwoven materials. The inventive combination and arrangement of the above-described selection of a hydrophobic nonwoven material towards the topsheet and the hydrophilic nonwoven material towards the backsheet produces, in comparison with all other combinations of materials, the shortest penetration time in conjunction with back-wetting which is lower by one order of magnitude.

BRIEF DESCRIPTION OF THE DRAWINGS

An examplary embodiment of the concept of the invention is illustrated in more detail by the figures, where.

Figure 1:
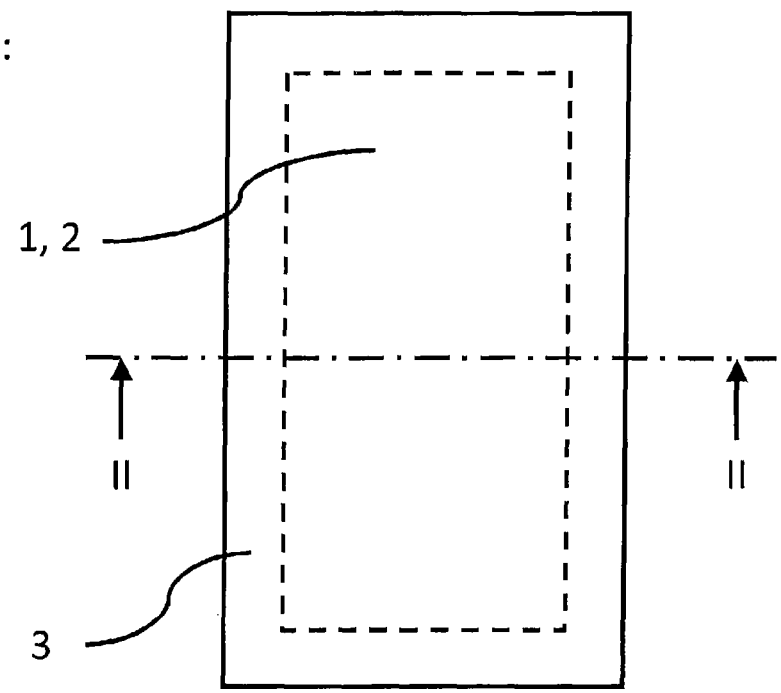
FIG. 1 shows a diagrammatic plan view of an absorbent hygiene product of the invention.
Figure 2:
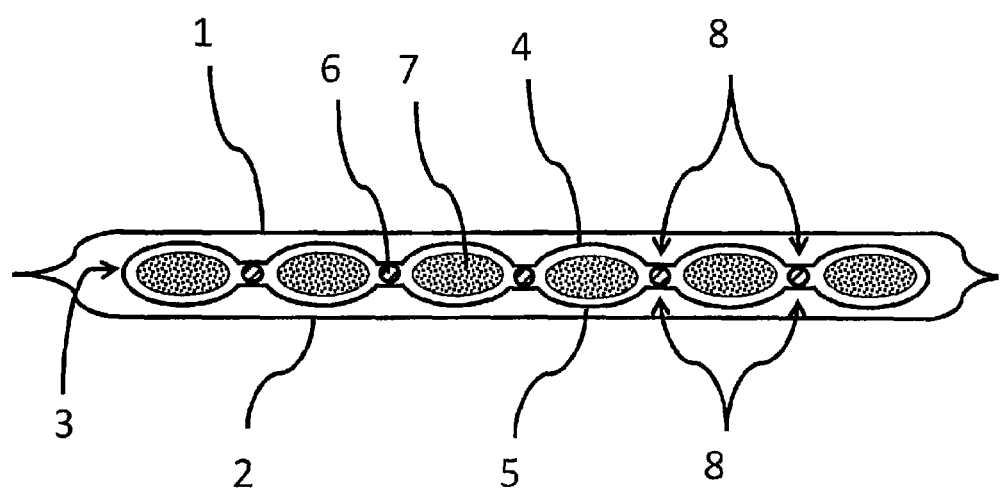
FIG. 2 shows a sectional view of the absorbent hygiene product shown in FIG. 1, along the line II-II in FIG. 1.

An absorbent hygiene product shown exemplarily in FIGS. 1 and 2 has a first outer ply, a topsheet (1) which faces the skin side of a wearer and consists usually of a hydrophilic material. It also has a further outer ply, a backsheet (2), which faces opposite the clothing side of the wearer and usually consists of a hydrophobic material.

Inserted between the topsheet (1) and the backsheet (2) is an absorbent laminate (3). The laminate (3) may be adheringly joined to the topsheet (1) and/or to the backsheet (2) of the product, this joining, like the joining of topsheet (1) and backsheet (2) as well, in a marginal region surrounding the laminate (3), taking place to one another, alternatively, in area, point or linear form by means of pressure-sensitive adhesive, welding, needling or other suitable fixing techniques or fixing means.

For certain applications it may also be advantageous to join and fasten only the topsheet (1) and the backsheet (2) to one another at least sectionally along one peripheral margin and to insert the absorbent laminate (3) loosely or merely attach it to the backsheet (2), in order not to hinder liquid acquisition through the topsheet (1) and to allow maximum swelling of the laminate (3) in all directions. It is also conceivable for the absorbent laminate (3) towards the backsheet side to bear at least regionally loosely against the backsheet (2).

Figure 3:
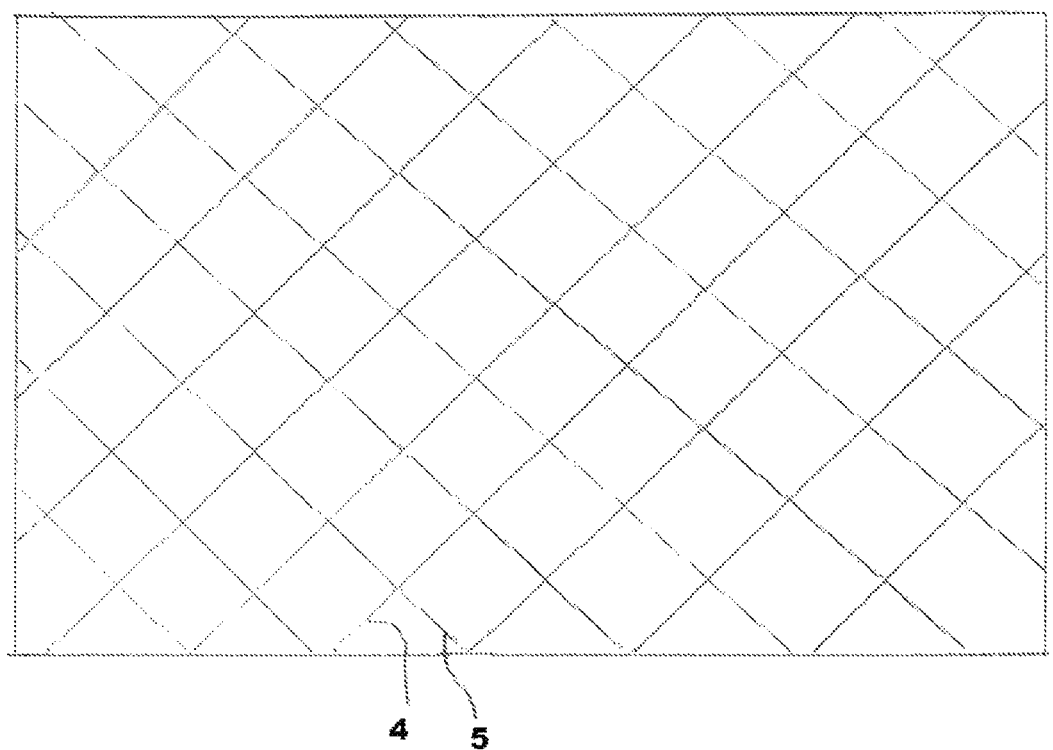
FIG. 3 shows a cross-sectional plan view of the absorbent hygiene product of the invention.

This absorbent laminate (3) consists of two flexurally yielding outer plies (4, 5), also as shown in FIG. 3, which are joined adheringly to one another with two diagonally intersecting plies, disposed between the plies (4 and 5), composed of pre-tensioned elastic filaments or tapes (6). The laminate (3) has a quilt-like structure, with superabsorbent granules or filaments (7) being incorporated in the open cassettes of this structure and consisting customarily of a superabsorbent polymer.

Embodiments and manufacturing methods for this laminate (3) which forms the absorption core are described for example in DE 10 2010 013 288.8, the content of which is incorporated in full into this description.

This absorption core may be attached with coinciding area to the topsheet (1) and/or backsheet (2) of the absorbent hygiene product, or else made narrower or broader in the transverse direction of the manufacture of the absorbent hygiene product, or applied in discrete individual sections in the longitudinal direction of manufacture ("Cut&Space").

Arranged and fixed on or in the absorbent hygiene product there may optionally be elastic closure systems, elasticized elements for optimizing the fit, additional components for improving handling, external barriers for the control of body fluids, etc.

Inventive and characteristic of the construction of the absorbent hygiene product is the partial reversal of the conventional model of "acquisition-distribution-storage" absorbent hygiene articles, and the displacement of a part of the fluid distribution function from the skin-side topsheet (1) to the clothing-side backsheet (2).

This is achieved by forming the outer ply (4) of the laminate (3) facing the topsheet (1), from a flexurally yielding hydrophobic material which sectionally or locally is made previous to fluids. This is accomplished preferably by means of heat, pressure, mechanical penetration, interaction with the pressure-sensitive adhesive, or by other suitable techniques allowing the hydrophobic material to be made regionally previous to fluid. One example of such is Corovin.

The outer ply (5) of the laminate (3), in contrast, facing the backsheet (2), is formed in accordance with the invention from a flexurally yielding material with a high transport capacity for fluids. Particularly suitable here are nonwovens, which are typically used as materials for wet wipes or as an acquisition/distribution layer (ADL) in infant nappies, examples being spunlace PET, PET viscose, viscose, PP nonwovens, carded, thermobonded hydrophilic polypropylene nonwovens, hygiene paper or comparable known materials. One example of such is Fibrella.

It is advantageous to generate this perviosity specifically in those sections in which the outer ply (4) facing the topsheet (1) and the outer ply (5) facing the backsheet (2) are joined adheringly to one another with the elastic threads (6), thus producing, in these sections subdivided by the elastic threads (6), a desired capillary effect by means on the one hand of a fine hole structure of the ply (4) facing the topsheet (1), and on the other hand of a wicking effect by the liquid transport qualities of the outer ply (5) of the laminate (3), facing the backsheet (2). Open cassettes of the laminate (3) that are formed as a result are additionally lined substantially hydrophobically on the skin side by the outer ply (4) that faces the topsheet (1), resulting here in a certain structural barrier to re-wetting on the skin side.

Another advantageous feature is that a multiplicity of open transport channels (8) are formed, as a result of the cassette form of the laminate (3), not only between the outer ply (4) facing the topsheet (1) and the topsheet (1) itself, but also, specifically, between the outer ply (5) facing the backsheet (2) and the backsheet (2) itself, these transport channels (8) being responsible for rapid distribution of the fluid in longitudinal and transverse direction of the absorbent hygiene product. Channel forming is also supported by the swelling of the laminate (3), and so, in contrast to commonplace absorbent hygiene products, the fluid distribution function of the absorbent hygiene product does not deteriorate, instead tending to improve, with increasing amount of fluid absorbed.

The entry of the fluid into the superabsorbent of the laminate (3) is supported by the transport capacity of the clothing-side outer ply (5), facing the backsheet (2), of the laminate (3), which supports the distribution of liquid in the backsheet-side transport channels (8) and passes on the fluid to the superabsorbent in the vertical direction.

What is claimed is:

1. An absorbent hygiene product for acquiring fluids, formed at least of a flexurally yielding topsheet and a flexurally yielding backsheet, inserted adheringly between which is an absorbent laminate, consisting of two flexurally yielding outer plies, incorporated adheringly between which are at least two diagonally intersecting, pre-tensioned plies of elastic filaments, and into which discrete sections of superabsorbent polymer have been incorporated, characterized in that one of the two flexurally yielding outer plies of the laminate faces the topsheet and is a hydrophobic material which in a region of adherence with the elastic filaments and the second outer ply has been locally or sectionally made fluid-pervious mechanically, chemically or thermally.

2. The absorbent hygiene product according to claim 1, characterized in that the topsheet-side outer ply of the laminate after 300 s fluid addition has a barrier effect of more than 2 cm for fluids.

3. The absorbent hygiene product according to claim 2, characterized in that the topsheet-side outer ply of the laminate after 300 s fluid addition has a barrier effect of more than 5 cm for fluids.

4. The absorbent hygiene product according to claim 1 characterized in that one of the two flexurally yielding outer plies of the laminate faces the backsheet and is a hydrophilic material having good fluid transport quality.

5. The absorbent hygiene product according to claim 4, characterized in that the backsheet-side outer ply of the laminate is a hydrophilic material having an areal distribution of more than 10 cm$^2$ wetted area by a fluid quantity of 1 ml applied pointwise.

6. The absorbent hygiene product according to claim 5, characterized in that the backsheet-side outer ply of the laminate is a hydrophilic material having an areal distribution of more than 20 cm$^2$ wetted area by a liquid quantity of 1 ml applied pointwise.

7. The absorbent hygiene product according to claim 1 characterized in that the laminate has cassette-like regions with superabsorbent polymer disposed therein.

8. The absorbent hygiene product according to claim 7, characterized in that a multiplicity of open transport channels are formed between the cassette-like regions of the laminate.

9. The absorbent hygiene product according to claim 1 characterized in that the absorbent laminate towards the topsheet side bears at least regionally loosely against the topsheet.

10. The absorbent hygiene product according to claim 1 characterized in that the absorbent laminate towards the backsheet side bears at least regionally loosely against the backsheet.

* * * * *